(12) United States Patent
Waisman

(10) Patent No.: US 7,094,236 B2
(45) Date of Patent: Aug. 22, 2006

(54) HYBRID INTERLOCKING PROXIMAL FEMORAL FRACTURE FIXATION

(76) Inventor: Marc Waisman, P.O. Box 5153, Kyriat Bialik 27151 (IL)

( * ) Notice: Subject to any disclaimer, the term of this patent is extended or adjusted under 35 U.S.C. 154(b) by 0 days.

(21) Appl. No.: 10/794,693

(22) Filed: Mar. 5, 2004

(65) Prior Publication Data

US 2004/0193156 A1 Sep. 30, 2004

Related U.S. Application Data

(60) Provisional application No. 60/457,216, filed on Mar. 25, 2003.

(51) Int. Cl.
A61B 17/56 (2006.01)
A61F 2/30 (2006.01)

(52) U.S. Cl. ...................................... 606/60

(58) Field of Classification Search .................. 606/53, 606/54, 60, 65, 66, 67, 104, 105, 62, 63, 606/64, 57, 58, 59, 68

See application file for complete search history.

(56) References Cited

U.S. PATENT DOCUMENTS 3,530,854 A * 9/1970 Kearney ...................... 606/67

(Continued)

FOREIGN PATENT DOCUMENTS

EP 0853923 A1 12/1997

(Continued)

OTHER PUBLICATIONS

Koval, Kenneth J., M.D., et al., *Clinical Orthopaedics and Related Research* No. 348, "Predictors of functional Recovery After Hip Fracture in the Elderly," 1998, pp. 22-28.

(Continued)

Primary Examiner—Eduardo C. Robert
Assistant Examiner—Anu Ramana
(74) Attorney, Agent, or Firm—Angenehm Law Firm; N. Paul Friederichs

(57) ABSTRACT

The present invention provides a unique and novel internal fixation for fixing an intracapsular and extracapsular including substochanteric fracture of a femoral neck while using minimal invasive procedure. The fixation comprises a hollowed or full tubular member having a sharp end and a blunt end that is adapted to be implanted while slightly crossing the fracture line. The tubular member is provided with three passages that extend from the sharp end to the blunt end. Three lag screws are adapted to pass through the passages and extend outwardly beyond said sharp end while thread that is provided in the lag screws so as to allow compression of fragments of the bone. The lag screws are provided with screw heads so as to prevent the screws from being fully inserted into the passages and through the trochanteric cortical bone.

The internal fixation can be incorporated into an external-interlocking fixation apparatus that comprises the tubular member laterally provided with bores on opposite sides of the tubular member wherein pin screws are adapted to be inserted through the bores so as to interlock the tubular member and additional pin screw that are nailed in a distal femoral fragment. A connecting member is adapted to secure the pin screws together so as to assure stability of the tubular member within the bone and to allow reduction, correction and fixation in the intra and post-operative period.

20 Claims, 8 Drawing Sheets

U.S. PATENT DOCUMENTS

| | | | |
|---|---|---|---|
| 3,678,925 A * | 7/1972 | Fischer et al. | 606/68 |
| 4,091,806 A * | 5/1978 | Aginsky | 606/63 |
| 4,612,920 A * | 9/1986 | Lower | 606/66 |
| 4,657,001 A * | 4/1987 | Fixel | 606/66 |
| 4,759,352 A * | 7/1988 | Lozier | 606/66 |
| 5,569,251 A * | 10/1996 | Baker et al. | 606/69 |
| 5,728,096 A | 3/1998 | Faccioli et al. | 606/54 |
| 5,743,912 A * | 4/1998 | Lahille et al. | 606/65 |
| 6,139,552 A * | 10/2000 | Horiuchi | 606/88 |
| 6,454,810 B1 * | 9/2002 | Lob | 623/23.47 |
| 6,511,481 B1 * | 1/2003 | von Hoffmann et al. | 606/67 |
| 6,517,542 B1 * | 2/2003 | Papay et al. | 606/73 |
| 6,607,561 B1 * | 8/2003 | Brannon | 623/23.11 |

FOREIGN PATENT DOCUMENTS

| | | |
|---|---|---|
| EP | 0940124 A1 | 3/1998 |
| WO | WO00/67653 | 11/2000 |

OTHER PUBLICATIONS

Jackson, Mark, et al., *Clinical Orthopaedics and Related Research* No. 399, "The Treatment of Nonunion After Intracapsular Fracture of the Proximal Femur," 2000, pp. 119-128.

* cited by examiner

HYBRID INTERLOCKING PROXIMAL FEMORAL FRACTURE FIXATION

This present application claims the benefit of earlier U.S. provisional patent application Ser. No. 60/457,216 filed on Mar. 25, 2003 by Waisman Marc and entitled "Hybrid Interlocking Proximal Femoral fracture Fixation".

FIELD OF THE INVENTION

The present invention relates to fracture fixation. More particularly, the present invention relates to hybrid interlocking proximal femoral fracture fixation.

BACKGROUND OF THE INVENTION

Internal fixation with nails and plates is a well-known surgical procedure used in orthopaedics and traumatology for stabilization of proximal femoral fractures. This procedure is considered as a classical open major surgery carrying out several possibilities of serious complications. It was considered in the past that rigidity of the fracture fixation site is advantageous, therefore, many of the available internal fixation devices are built so as to eliminate all movements (except of sliding possible motion) at the fracture site. It is now generally accepted that some micro-movements at the fracture site are essential for better fracture healing and even for stimulating callus formation. However, this conception is not valid for intracapsular femoral neck fractures.

Internal fixation bears many disadvantages including the fact that the surgery is highly expensive and complex, which may be complicated by significant blood loss and infection. There is a lack of ability to perform post-operative re-fixation, the morbidity and mortality rates are high and as a consequence of the surgery, there is a prolonged hospitalization related to peri-operative complications. The death rates following internal fixation in cases of subcapital (intracapsular) fractures are intimidating: 3% in the hospital, 25% at one year and additional 40% at two years following the surgery. 30% experience avascular necrosis, 43% non-union and 50% experience peri-operative-postoperative local and systemic complications. The data is collected from Clinical Orthopaedics and Related Research 348:22–28, 1998; Clinical Orthopaedics and Related Research 399: 119–128, 2002. These papers are incorporated herein as references; however, similar results were established and published in many other scientific reviewed publications. The consequences of intertrochanteric-pertrochanteric (extracapsular) fractures are no less frightening. 15% experience fixation failure, 10% dies at one year; 20% at two year, 20% complicated with infection, and 30% with mal-union. Similar consequences are found in subtrochanteric fractures.

External fixation using nails and screws connected to the femoral head, neck, and shaft through an external device provides the possibility to stabilize the fracture. This procedure is done using minimal invasive interventional surgery.

Clinical evidences clearly indicate that stabilization of a peritrochanteric femoral neck fracture by external fixation markedly reduces mortality, reduces the incidence of severe complications and improve fracture outcomes at the immediate postoperative time in comparison with the classical internal fixation. External fixation has other advantages such as decreased length of hospitalization and medical costs, reduces post-operative fracture pain, facilitates the access to the patient nursering care, reduces need for forced recumbency as well as risk of pressure sores, pulmonary embolism, pulmonary infection etc. External fixation is a safe and reliable method of achieving osseous stability in trochanteric femoral fractures. Generally, external fixation imparts versatility, ease to apply with minimal operative time, bleeding and tissue injury.

A percutaneous connection of a fractured upper part of the femur is disclosed in U.S. Pat. No. 5,429,641. Another example of an external trochanter splint is disclosed in U.S. Pat. No. 5,728,096. European patent application EP 0940124A1 teaches an external fixation device with changeable angle for trochanteric fractures. The devices that are disclosed herein as references as well as other similar devices for external fixation of trochanteric femoral fractures have many disadvantages and complications. One of the dangerous occurrences is the penetration of the neck screws into the acetabulum due to severe osteoporosis. Other disadvantages are hardware failure, the device is fixed in a lateral posterior bulging position that is uncomfortable, and there is an immense difficulty in the supine or sitting position of the patient.

It is a long felt need to provide an external device that eliminates the severe disadvantages of the available devices for external fixation of pentrochanteric fractures, which is one of the fixations that results in several complications.

As for the internal fixation, specially designed screws were developed, for example a screw member that is disclosed in PCT application published as WO00/67653, an intramedullary cavity nail disclosed in EP 0853923, or an anchor that is disclosed in U.S. patent application No. 2002/0143333. Another commercially available fixation is sold by Fixano s.a. by the commercial name osteosynthesis of unstable femoral neck fractures by D.S.S. system (double sliding screws).

SUMMARY OF THE INVENTION

It is an object of the present invention to provide a hybrid interlocking proximal femoral fracture fixation that enables minimal invasive fracture fixation. In this way, early callus formation in extracapsular fractures occurs.

It is another object of the present invention to provide an internal fixation for femoral neck intracapsular fractures that exhibits continuous compression by sliding properties.

It is yet another object of the present invention to provide a hybrid interlocking proximal femoral fracture fixation that combines a new and unique internal nail and an external non-rigid fixator, for extracapsular fractures.

An additional object of the present invention is to provide a fixation technique that is easy to use, and requires relatively short and minimal procedure for the surgeon.

It is therefore provided in accordance with one aspect of the present invention, an internal fixation for fixing an intracapsular fracture of a femoral neck, comprising:

a tubular member having a sharp end and a blunt end;

at least one passage provided in said tubular member wherein said at least one passage extends from said sharp end to said blunt end;

at least one screw adapted to pass through said at least one passage and extend outwardly beyond said sharp end;

thread provided in a portion of said at least one screw that is adapted to extend beyond said sharp end;

screw head is provided in said at least one screw so as to prevent said at least one screw from being fully inserted into said at least one passage;

Whereby after said tubular member is implanted in the bone crossing in about 1 or 2 millimeters the fracture line, said at least one screw is inserted through said at least one passage so that compression of fragments of the bone is maintained in order to facilitate the healing process.

Furthermore, in accordance with another preferred embodiment of the present invention, said tubular member is a hollow tube.

Furthermore, in accordance with another preferred embodiment of the present invention, said hollow tube is provided with a profile such as a circular, oval, triangular, or rectangular profile.

Furthermore, in accordance with another preferred embodiment of the present invention, said hollow tube is provided with holes.

Furthermore, in accordance with another preferred embodiment of the present invention, said hollow tube can be filled with bone grafting materials so as to promote bone healing.

Furthermore, in accordance with another preferred embodiment of the present invention, said tubular member combined with said at least one screw perform compression and sliding motion.

Furthermore, in accordance with another preferred embodiment of the present invention, three lag screws are provided to correspond three passages that are provided in said tubular member.

Furthermore, in accordance with another preferred embodiment of the present invention, said tubular member is inserted to the femoral neck in an angle of about 95–110 degrees in respect with an axial line of the femoral shaft so that an inferior screw of said three lag screws is positioned in a direction of an the inferior quadrant of the femoral head so as to slightly touch a the strong cortical bone of a calcar femori of the femoral neck.

Furthermore, in accordance with another preferred embodiment of the present invention, said three screws are adapted to penetrate an inferior quadrant of the femoral head, preferable distally of the teres ligament vascularity.

Furthermore, in accordance with another preferred embodiment of the present invention, wherein said tubular member is provided with bone substitutes allowing bone grafting into said tubular member.

Furthermore, in accordance with another preferred embodiment of the present invention, said fixation is further interlocked with external fixator.

It is further provided in accordance with another aspect of the present invention, a hybrid interlocking fixation apparatus for fixating a fracture in the femoral neck or the peritrochanteric region, the apparatus comprising.

a tubular member having a sharp end and a blunt end;
at least one passage provided in said tubular member wherein said at least one passage extends from said sharp end to said blunt end;
at least one screw adapted to pass through said at least one passage and extend outwardly beyond said sharp end;
at least two bores are laterally provided on said tubular member wherein said at least two bores are provided on opposite sides of said tubular member;
at least four pin screws wherein at least two pin screws are adapted to interlock said tubular member and said at least two pin screws and at least two pin screw are nailed in a distal bone fragment so as to assure stability of the tubular member within the bone;
a connecting member adapted to secure said at least two pin screws together;

whereby said tubular member is implanted in the femoral neck, said at least one screw is inserted through said at least one passage so that compression and sliding of the fractured fragments is maintained, at least one pin screw is nailed through said tubular member through said at least two bores and at least two pin screw is pined in said distal bone fragment wherein the pin screws are interconnected by said connecting member in order to facilitate the healing process and wherein said connecting member's connections can be corrected post-operatively.

Furthermore, in accordance with another preferred embodiment of the present invention, three passages are provided in said tubular member.

Furthermore, in accordance with another preferred embodiment of the present invention, three screws are provided to pass through said three passages.

Furthermore, in accordance with another preferred embodiment of the present invention, six bores are provided in said tube wherein said six bores are organized so that three of the six bores are provided opposite other three of said six bores and wherein three pin screws are adapted to be inserted through said six bores from one side of said tubular member to another side.

Furthermore, in accordance with another preferred embodiment of the present invention, said connecting member comprises two clamps and rotating screwing rods, and wherein one clamp clamps the screw pins that are nailed to the distal bone fragment and a second clamp clamps the screw pins that are screwed into said tubular member.

Furthermore, in accordance with another preferred embodiment of the present invention, a distance between said one clamp and said second clamp is changeable by rotation of said rotating screwing rods that are connected to each clamp by two bolts having spherical head wherein said rotating screwing rods are screwed onto said two bolts.

Furthermore, in accordance with another preferred embodiment of the present invention, malpositioning of the hybrid interlocking fixation is corrected in intra and post-operative period.

Furthermore, in accordance with another preferred embodiment of the present invention, said tubular member is provided with a plurality of small wall holes.

Furthermore, in accordance with another preferred embodiment of the present invention, the apparatus is provided with radiolucent materials or other metals.

Furthermore, in accordance with another preferred embodiment of the present invention, the apparatus can be disposable.

Furthermore, in accordance with another preferred embodiment of the present invention, said tubular member is provided with bone substitutes allowing bone grafting into said tubular member.

And in accordance with yet another aspect of the present invention is provided a method for fixing an intracapsular fracture of a femoral neck, the method comprising:
providing an internal fixator comprising
a tubular member having a sharp end and a blunt end;
at least one passage provided in said tubular member wherein said at least one passage extends from said sharp end to said blunt end;
at least one screw adapted to pass through said at least one passage and extend outwardly beyond said sharp end;
thread provided in a portion of said at least one screw that is adapted to extend beyond said sharp end;
screw head is provided in said at least one screw so as to prevent said at least one screw from being fully inserted into said at least one passage;

performing 2–3 cm long skin incision at the trochanter region;

inserting said tubular member to the femoral neck in an angle of about 95–110 degrees in respect with an axial line of the femoral shaft so that an inferior screw of said at least one lag screws is adapted to be positioned in a direction of an inferior quadrant of the femoral head so as to slightly touch a strong cortical bone of the calcar femori, wherein said tubular member is crossing in about 1 or 2 millimeters the fracture line;

screwing said at least one lag screw.

Furthermore, in accordance with another preferred embodiment of the present invention, the method further comprising:

providing at least two bores on said tubular member wherein said at least two bores are provided on opposite sides of said tubular member;

interlocking at least two pin screws in said at least two bores;

nailing at least two pin screws in a distal bone fragment;

providing a connecting member adapted to secure the pin screws together.

Additionally, in accordance with another preferred embodiment of the present invention, the method further comprising correction, reduction and fixation in intra and post-operative period.

BRIEF DESCRIPTION OF THE FIGURES

In order to better understand the present invention and appreciate its practical applications, the following Figures are attached and references herein. Like components are denoted by like reference numerals.

It should be noted that the figures are given as examples and preferred embodiments only and in no way limit the scope of the present invention as defined in the appending Description and Claims.

DETAILED DESCRIPTION OF THE INVENTION AND THE FIGURES

The present invention provides a new and unique femoral fracture fixation that comprises an internal fixator and an external fixator. Basically, the internal fixator for an intracapsular fracture of a femoral neck comprises a tubular member having a sharp end and a blunt end. The tubular member can be a hollow member or a solid member. At least one passage extending from the sharp end to the blunt is provided in the tubular member wherein the passages are adapted to accommodate lag screws. The screws are adapted to extent outwardly beyond said sharp end and into the bone so that compression of the fracture is maintained in order to facilitate the healing process, therefore, the portion of the screws that extend beyond the sharp end is provided with a thread. It is preferable to provide 3 passages and corresponding lag screws. The tubular member will be referred in this text also as a nail-cage. The nail-cage and the lag screws can be used as "stand alone" as a novel and unique internal fixator of intracapsular femoral neck fractures and as an alternative for the classic cannulated screws, allowing bone grafting into the nail-cage. The nail-cage and the lag screws are mainly intended for Garden 1–2 and 3 subcapital femoral fractures.

The nail-cage is inserted into the bone in a minimal invasive surgery. The nail-cage is inserted preferably through a 2–3 cm long skin incision. The external parts of the fixator are suitable to be removed in the out-patient follow up, without anesthesia. The external parts of the device are preferably made of titanium or other radiolucent materials such as aluminum 70 that is approved by FDA and are optionally disposable.

Figure 1:
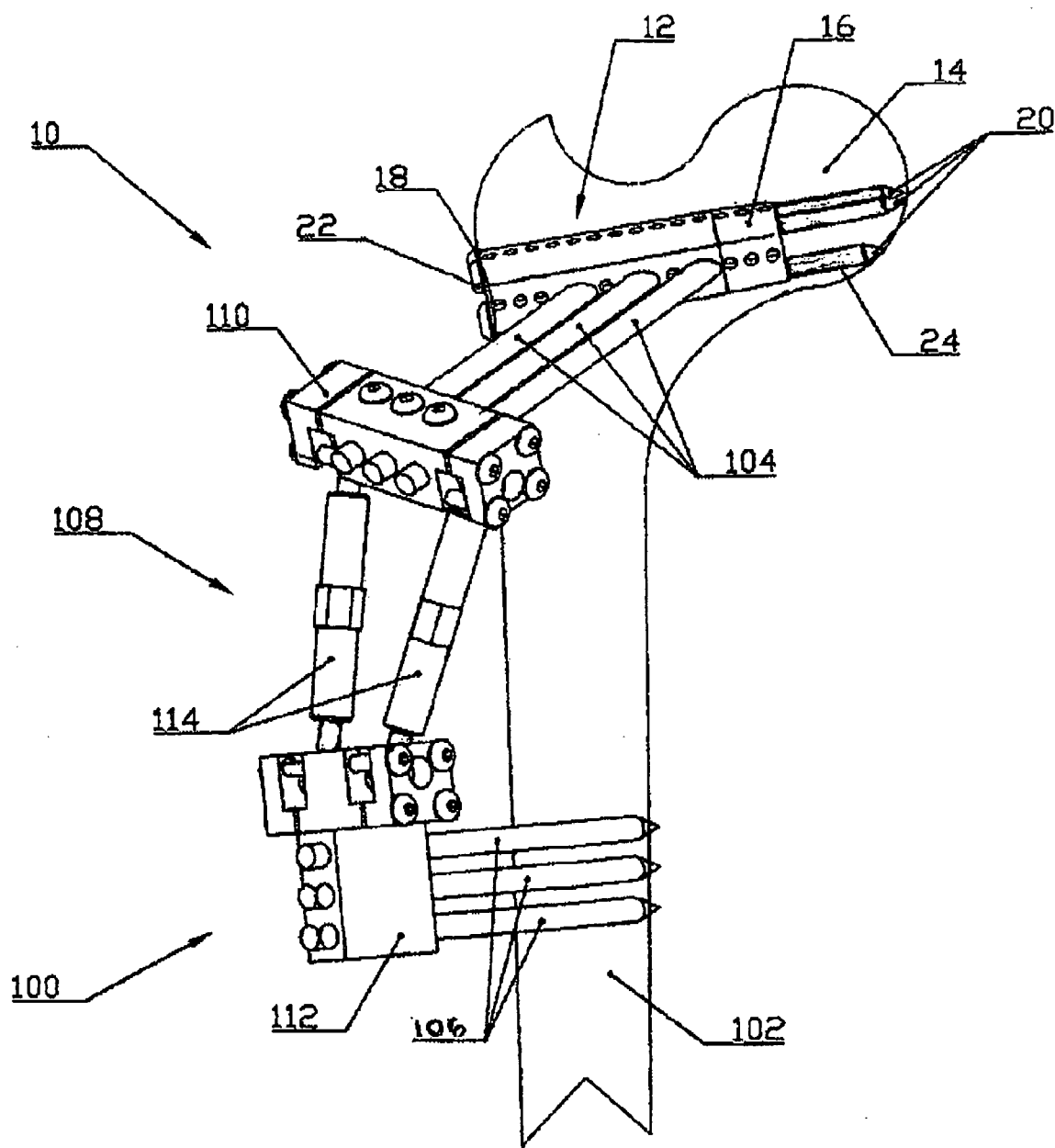
FIG. 1 illustrates an isometric view of a hybrid interlocking proximal femoral fracture fixation in accordance with a preferred embodiment of the present invention, and its positioning in a femoral bone.

Reference is now made to FIG. 1 illustrating an isometric view of a hybrid interlocking proximal femoral fracture fixation in accordance with a preferred embodiment of the present invention, and its positioning in a femoral bone. The femoral bone and especially its neck are subjected to severe injuries that are difficult to fixate. Generally, the fracture fixation device of the present invention is a combination of internal and external fixation by interlocking system that connects the fractured upper fragment to the femoral shaft by a modular fixator. It is possible to correct the postoperative positioning in any case of varus or valgus deformity, rotation angulation shortening by distraction, compression, rotation, angulation, or translation. Causes for malpositioning can be related to unskilled operative technique as well as to low bone quality.

Hybrid device 10 comprises a nail-cage 12 that is adapted to be implanted inside the femoral neck 14. Nail-cage 12 is preferably a hollow tubular member having a sharp end 16 and a blunt end 18. Optionally, the member can be a full structure instead of hollow. The hollow in nail-cage 12 allows drainage through the center hole of the nail so as to reduce the high pressure intracapsular hemarthrosis that develops from the fracture hemorrhage. The drainage reduces damage to the poor remaining vascularity and consequently reduces one of the common causes of avascular necrosis in the femoral head. Nail-cage 12 is inserted while crossing the fracture line by about 1–2 mm and allows bone grafting into the cage with autograft, allograft or other bone substitute.

Preferably three compression screws 20 (lag screws) are adapted to pass through nail-cage 12 from its blunt end 18 to its sharp end 16 so that the screws are extended proximally through the sharp end and screwed inside the bone. The extension of the screws beyond nail-cage 12 provides minimal metal volume penetration to the femoral head using only the three lag screws up to the subchondral bone. Minimal metal volume penetration prevents or avoids further damage to the vascularity in the femoral head. Each compression screw 20 is provided with a screw head 22 that prevents the screw from totally advancing into nail-cage 12. Compression screws 20 are used to compress the fracture so as to assure fast healing. The nail cage combined with the compression screws are adapted to perform sliding motion as well as compression. The compression is performed from blunt end 18 of the nail and the screw heads, anchoring the lateral trochanteric cortical bone around the blunt end of the nail-cage. The extended portion of compression screws 20 is provided with thread 24 so as to facilitate the compression process. Nail-cage 12 and compression screws 20 provide the possibility to introduce chip bone grafting up to the fracture line due to the nail's unique and special structure. In the case the nail-cage is hollow, the interior of nail-cage 12 can be filled with bone grafting materials so as to promote rapid bone healing.

Nail-cage 12 is inserted into the femoral neck by minimal invasive procedure. The optimal angle of penetration of the nail-cage and the screw is between 100 to 110 degrees in respect of the femoral axis. In this way, the inferior screw of compression screws 20 is positioned so that it slightly touches the strong cortical bone of the calcar femori. All three compression screws 20 penetrate only the inferior half of the femoral head, preferable distally of the teres ligament vascularity, avoiding damage to the capilar spongeous intraosseous circulation and further reduce the possibility of avascular necrosis.

External fixator 100 connects nail-cage 12 to the distal bone fragment 102. External fixator 100 comprises preferably six pin-screws from which three pin-screws 104 are pined into nail-cage 12 and additional three pin screws 106 are pined in distal bone fragment 102. All six pin-screws, 104 and 106, are interconnected in a connecting member 108 comprising an upper clamp 110, which clamps pin-screws 104, and a lower clamp 112, which clamps pin-screws 106. Connecting member 108 further comprises preferably two rotating screwing rods 114 that connect upper clamp 110 and lower clamp 112. rotating screwing rods 114 have changeable length and connect the clamps in a manner that allows a certain degree of freedom in the positioning of the clamps in respect with each other. A comprehensive description is provided herein after.

Figure 2A:
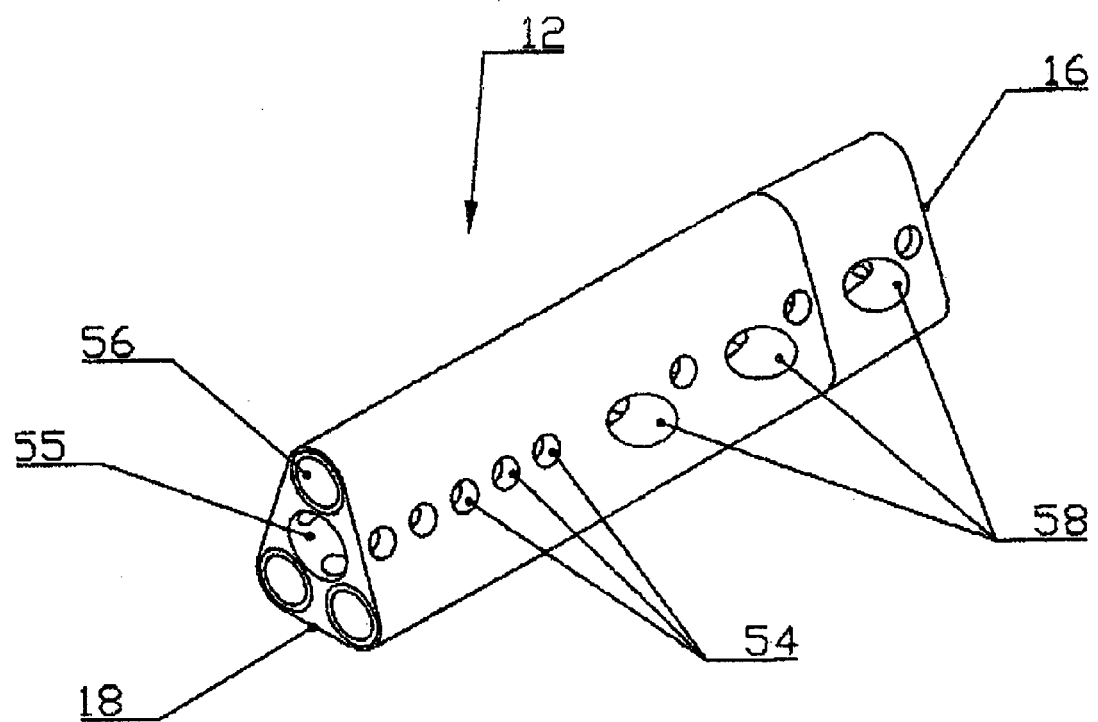
FIGS. 2a–c illustrate views of a nail-cage implant in accordance with a preferred embodiment of the present invention.
Figure 2B:
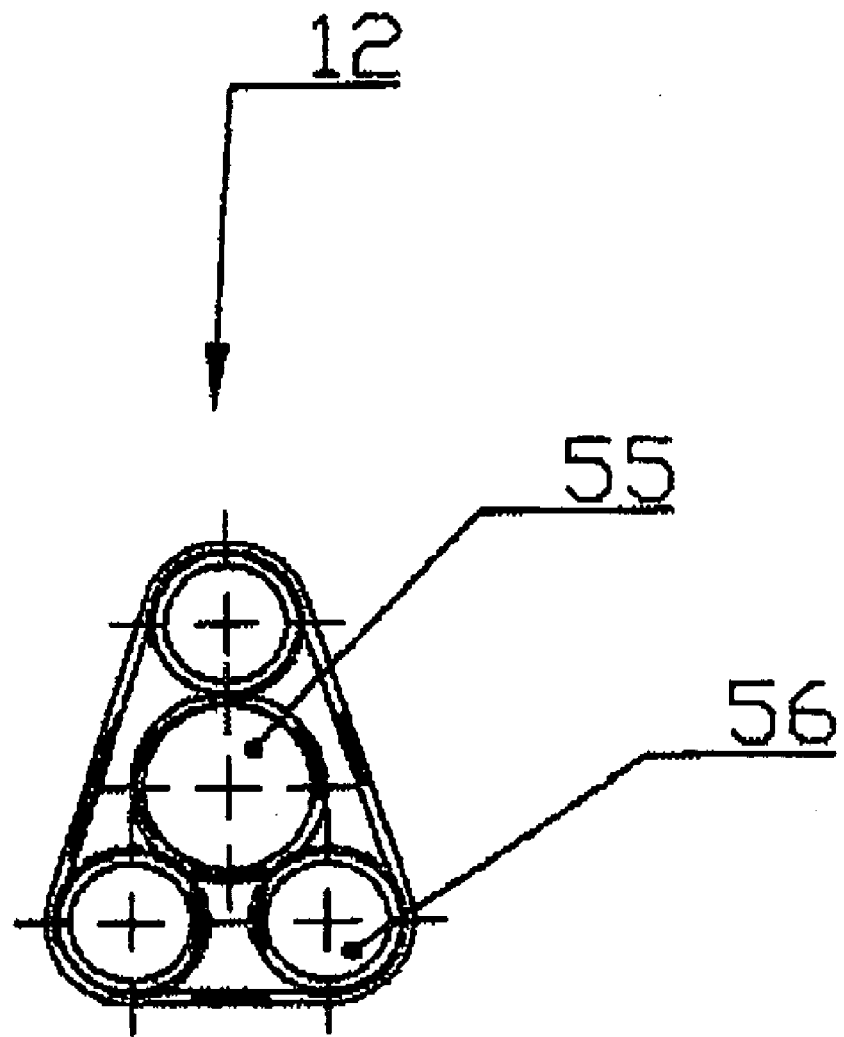
Figure 2C:
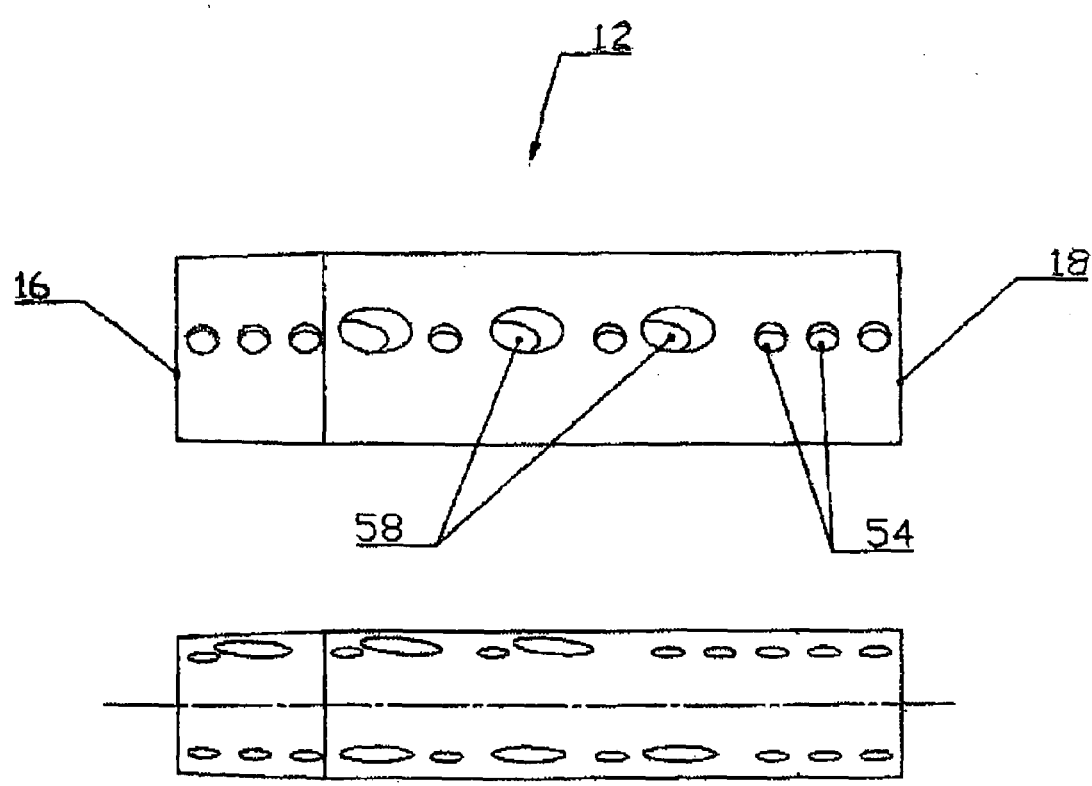

Reference is now made to FIGS. 2a–c illustrating views of a nail-cage implant in accordance with a preferred embodiment of the present invention. The nail cage implant is adapted to be incorporated in the hybrid interlocking fixation of the present invention. Nail-cage 12 is a hollow tubular member having a triangular profile that is provided with sharp end 16 and blunt end 18 and a hollow 55 that passes through the nail. Nail-cage 12 is adapted to be inserted to the femoral neck by forcing it into the bone through sharp end 18. Nail-cage 12 is preferably made of a biocompatible metal such as titanium. The nail-cage can be left in place in case of bone grafting or removed after the bone is healed; however, the nail-cage as well as the compression screws that pass through it may be made from a biodegradable material.

It is preferable to provide the wall of nail-cage 12 with a plurality of relatively small holes 54 so as to allow the bone to grow into the nail-cage 12 in order to allow contact and bone growing together with the grafting materials. It is optional to introduce autologous bone graft or osteoconductive-osteoinductive materials into nail-cage 12 (not shown in the Figures) so as to encourage bone grow.

Nail-cage 12 is provided with passages and preferably three passages 56 that pass through the wall of the tube and extend from sharp end 16 to blunt end 18. Passages 56 are provided with openings at both the sharp end and the blunt end through which compression lag screws 20 (shown in FIG. 1) may be screwed after the implantation of nail-cage 12. The nail cage of the present invention has the properties of compression and sliding when it is combined with the three lag screws.

Figure 6:
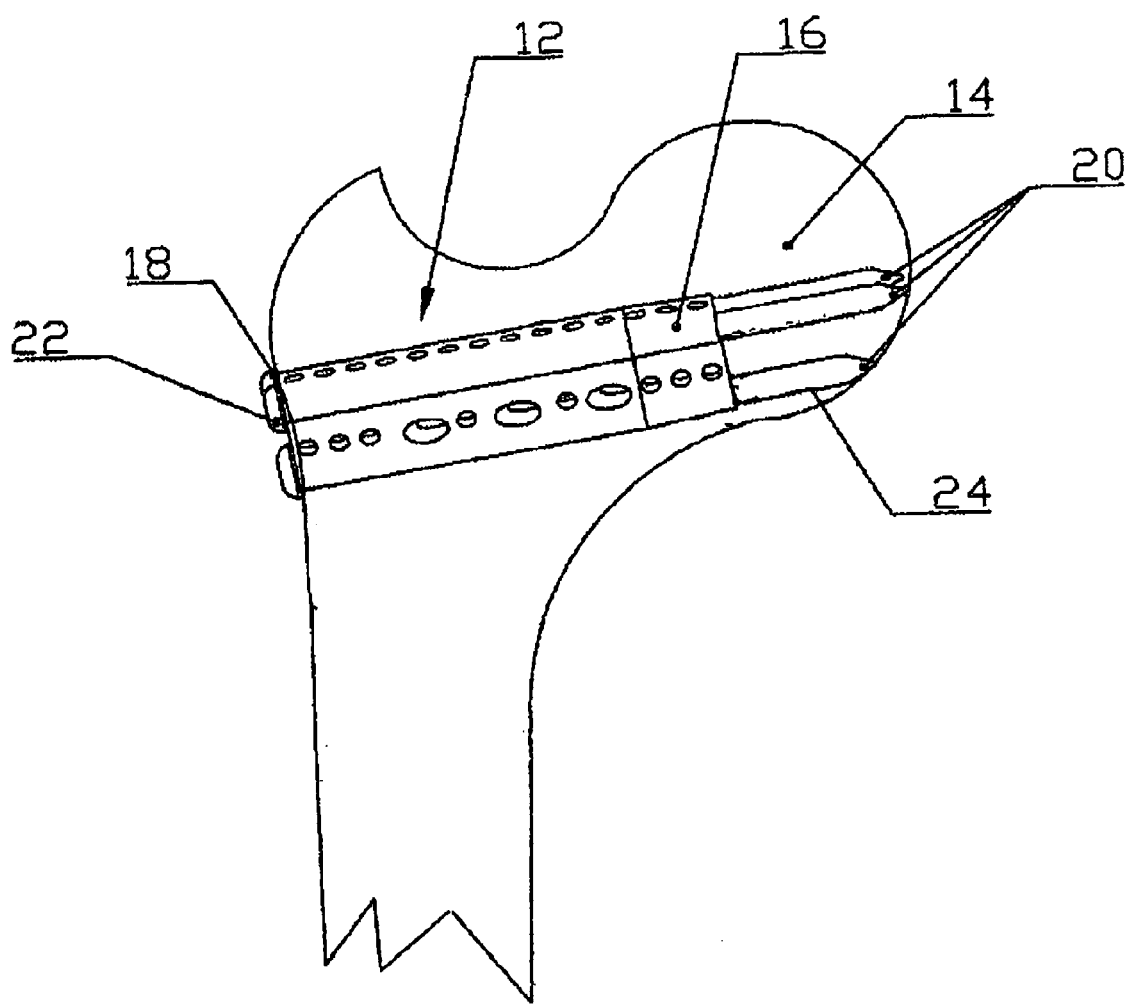
FIG. 6 illustrates an isometric view of the nail-cage implant fixed in an internal fixation in accordance with a preferred embodiment of the present invention.

Reference is now made to FIG. 6 illustrating illustrates an isometric view of the nail-cage implant fixed in an internal fixation in accordance with a preferred embodiment of the present invention. Nail-cage 12 is implanted within a femoral bone 13 while three lag screws 20 are interlocked within nail-cage 12.

Returning to FIG. 2, nail-cage 12 is further provided with bores, and preferably six bores wherein three bores 58 are provided in a row on one side of the tube while the other three bores (can not be seen in the Figures) are provided in a row opposite three bores 58. Both opposite rows of bores are shifted in respect with each other, e.g. one row is closer to blunt end 18 and three bores 58 are closer to sharp end 16. All bores are provided with an external thread so as to allow compatible screws to be screwed through them. The bores are adapted to receive three pin screws 104 of the external fixation (shown in FIG. 1) to be screwed through them from one side to the other while maintaining a predetermined angle between the nail cage and the pin screws.

Figure 3:
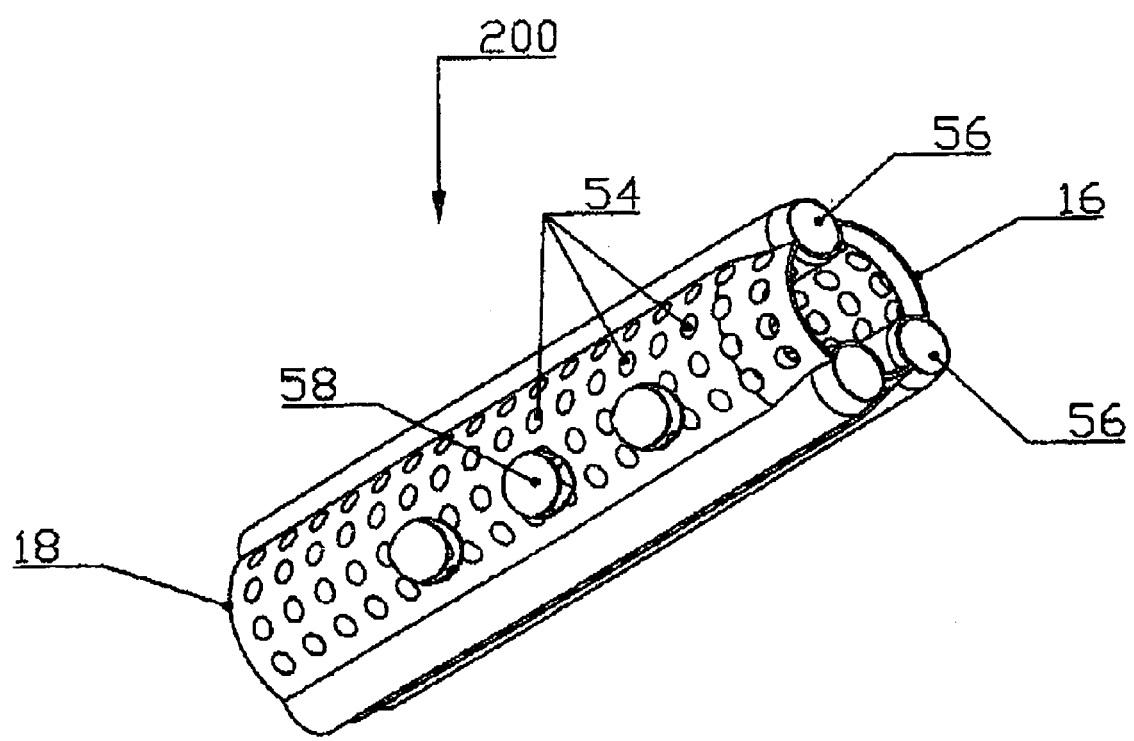
FIG. 3 illustrates an isometric view of a nail cage implant in accordance with another preferred embodiment of the present invention.

Reference is now made to FIG. 3 illustrating an isometric view of a nail cage implant in accordance with another preferred embodiment of the present invention. Nail-cage 200 is a hollow tubular member having a circular profile. Similarly to the nail-cage shown herein before, nail-cage 200 is provided with a sharp end 16 adapted to be pushed into the bone and a blunt end 18. preferably three passages 56 adapted to receive lag screws (the screws are not shown in the Figure).

Returning to FIG. 1, it is clearly shown that three compression screws 20 are inserted through passages 56 and three pin screws 104 are inserted through six lateral bores 58 and 60. As mentioned herein before, pin screws 104 are interconnected to pin screws 106 that are nailed into distal bone fragment 102. Pin screws 104 are connected to nail-cage 12 in an angle that directs the external fixation to anterior and lateral directions. In this way, the external fixation protrudes in the anterolateral proximal part of the patient's thigh, without disturbing the hip flexion or the lying supine patient position.

It is important to notice that the nail-cage can be implanted in order to fixate a fracture in the femoral neck using the compression lag screws without employing the external fixation as shown in FIG. 6.

Figure 4:
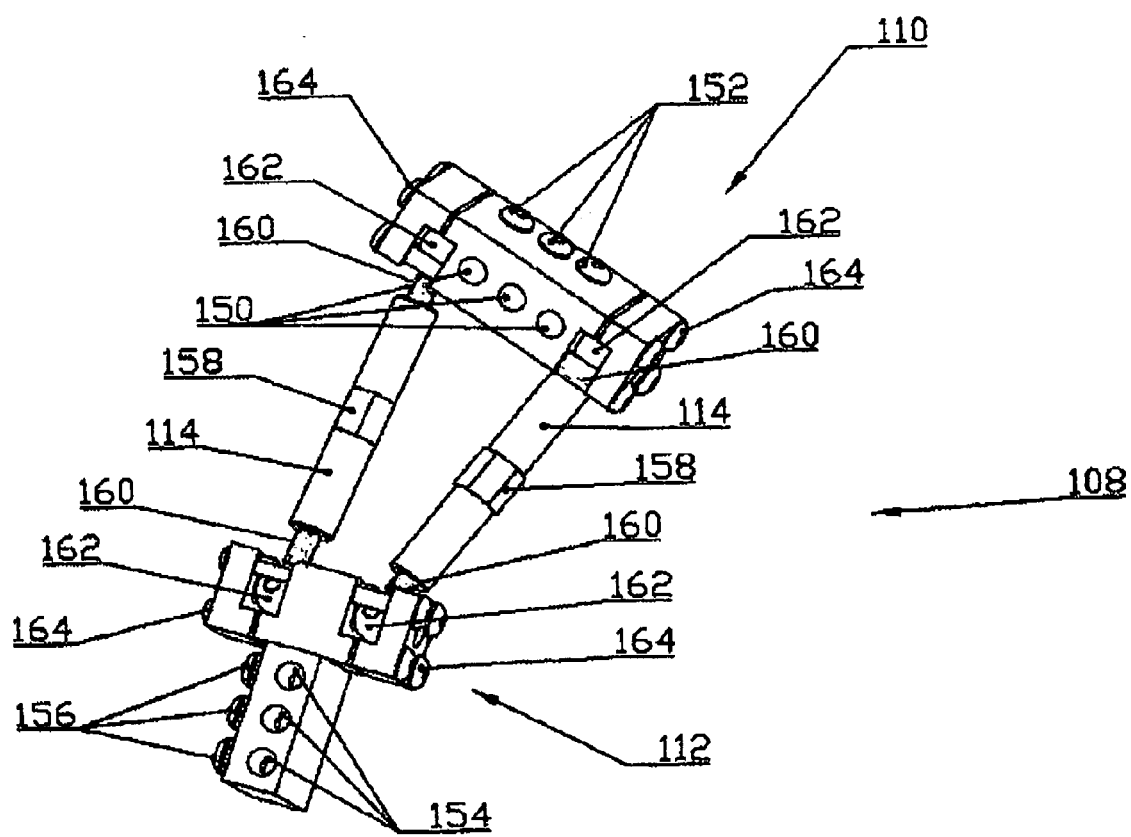
FIG. 4 illustrates an isometric view of a connecting member in accordance with a preferred embodiment of the present invention, connecting the external fixation.
Figure 5:
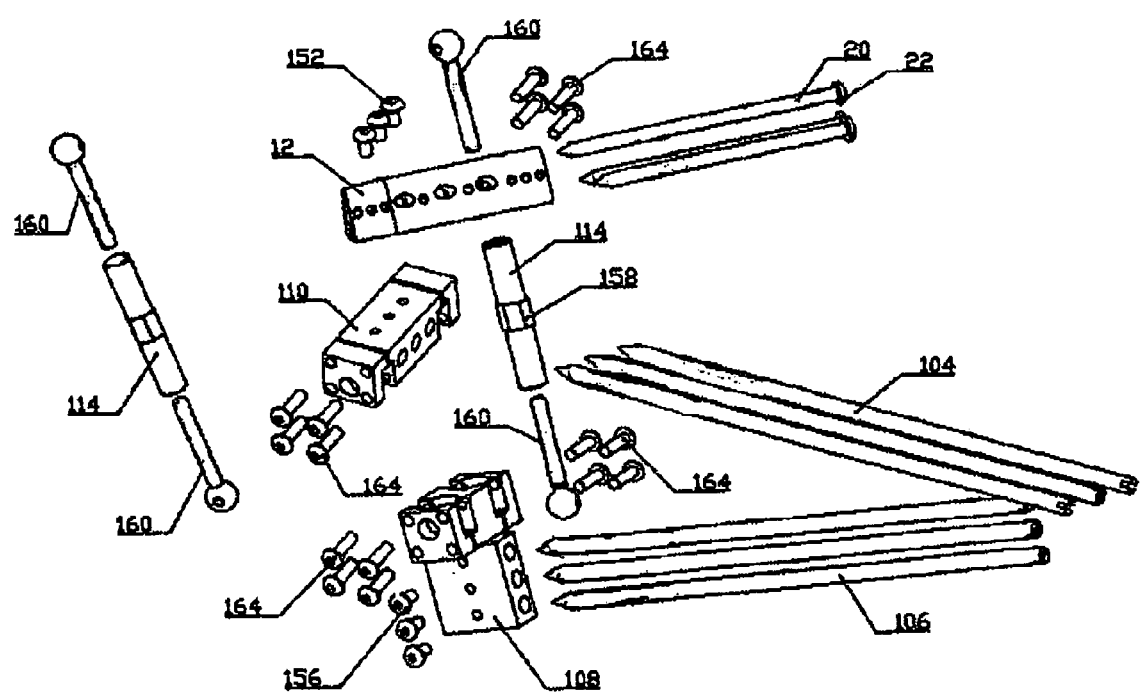
FIG. 5 illustrates an exploded view of the hybrid interlocking proximal femoral fracture fixation shown in FIG. 1.

Reference is now made to FIG. 4 an isometric view of a connecting member in accordance with a preferred embodiment of the present invention, connecting the external fixation. The connecting member is a part of the external fixation of the present invention. Connecting member 108 is adapted to externally fixate and support the nail-cage that is implanted within the femoral neck. Connecting member 108 is designed so as to allow intra and post-operative corrections. Therefore, connecting member 108 comprises an upper clamp 110, which clamps pin-screws 104, and a lower clamp 112, which clamps pin-screws 106 (the pin-screws are not shown in FIG. 3). connecting member 108 further comprises preferably two rotating screwing rods 114 that connect upper clamp 110 and lower clamp 112.

Upper clamp 110 is provided with three bores 150 that are compatible to allow pin screws 104 to pass through them. Pin screws 104 are fastened in bores 150 using three Allen screws 152 (the pin screws are not shown in FIG. 3). In a similar manner, a portion of lower clamp 112 is provided with three bores 154 through which pin screws 106 (not shown in the figure) can be inserted and fastened using three Allen screws 156.

rotating screwing rods 114 that connect upper clamp 110 and lower clamp 112 are preferably tubes provided with inner threads and preferably hexagonal aid 158 that facilitates rotation of rotating screwing rods 114 so as to adjust the distance and the angles between upper clamp 110 and lower clamp 112. rotating screwing rods 114 are provided with bolts 160 that are screwed inside the tubes through all four openings of the tubes. Each bolt 160 is provided with a spherical head 162 wherein the spherical head is firmly held in the corresponding clamp. Rotating screwing rods 114 about their elongated axis when the bolts heads are held in the clamps changes the distance between the two clamps so as to enable changes in the orientation of the external fixation post-operatively. Each bolt head 162 is held in the clamp in a recess that is adapted to be compressed onto the bolt head using Allen screws 164. When the physician wants to change the angle of rotating screwing rods 114 in regard with the clamps, he releases Allen screws 164 so that the spherical heads can rotate in the clamp's recess. In the right position, the physician fastens Allen screws 164. It is important to notice the minimal use of parts so as to facilitate the work of the surgeon with the device of the present invention.

Reference is now made to FIG. 4 illustrating an exploded view of the hybrid interlocking proximal femoral fracture fixation shown in FIG. 1. It is clearly shown that the amount of parts that comprise the apparatus of the present invention is minimal and effective. Nail cage 12 is adapted to be implanted in the femoral neck and receive compression screws 20. There are cases in which the internal fixation is enough and there is no need in the external fixation. In cases the external fixation is required; pin screws 104 are inserted through nail cage 12 while pin screws 106 are nailed into the distal bone fragment. The pins are interconnected in the connecting member that comprises clamps 110 and 108 as well as rotating screwing rods 114. One of the important features of the connecting member of the present invention is in its versatility using only Allen screws and length changes in the rotating screwing rods.

The device of the present invention is intended to be used for intracapsular and extracapsular (including subtrochanteric) femoral fractures.

One of the important features of the hybrid interlocking fixation apparatus of the present invention is that the procedure of the present invention is of minimal invasive surgery instrumentations, mainly based on using multiple tissues penetrations by pin-screws. This fact facilitates the use of robotics for fast, exact, and controlled operative steps.

The external parts of the hybrid interlocking fixation apparatus are suitable for removal in the outpatient follow-up without anesthesia. The internal nail-cage and screws may be left in place. The nail-cage and screws can be made of bio-resorbable materials that are resorbed after some time.

The parts of the fixator that are inserted into the body can be made with radiolucent materials so as to facilitate the x-ray imaging follow-up of the bone healing process.

It is optional to provide the device of the present invention with disposable parts so as to reduce the costs.

It should be clear that the description of the embodiments and attached Figures set forth in this specification serves only for a better understanding of the invention, without limiting its scope as covered by the following Claims.

It should also be clear that a person skilled in the art, after reading the present specification can make adjustments or amendments to the attached Figures and above described embodiments that would still be covered by the following Claims.

The invention claimed is:

1. An internal fixation device for fixing an intrecapsular fracture of a femoral neck, comprising:
   a tubular member having a sharp end and a blunt end;
   at least one first passage provided in said tubular member and at least one second passage provided in a sidewall of said tubular member wherein said at least one first passage and said at least one second passage extends from said blunt and to said sharp end;
   at least one screw adapted to pass through said at least one second passage end extend outwardly beyond said sharp end;
   thread provided in a portion of said at least one screw that is adapted to extend beyond said sharp end;
   screw head is provided in said at least one screw so to prevent said at least one screw from being fully inserted into said at least one second passage;
   whereby tubular member that implanted in the bone crosses the fracture line by at least 1 millimeter, and said at least one screw are inserted through said at least one second passage so that compression of fragments of the bone is maintained in order to facilitate the healing process; and wherein said at least one screw are three lag screws that are provided to correspond to said at least one second passage that are three passage provided in said sidewall of said tubular member.

2. The internal fixation device as claimed in claim 1, wherein said tubular member is a hollow tube.

3. The internal fixation device as claimed in claim 2, wherein said hollow tube is provided with a profile such as circular, oval, triangular, or rectangular profile.

4. The internal fixation device as claimed in claim 1, wherein said at least one first passage is filled with bone grafting material so as to promote bone healing.

5. The internal fixation device as claimed in claim 1, wherein said tubular member combined with said at least one screw perform compression and sliding motion.

6. The internal fixation devise as claimed an claim 1, wherein said tubular member is inserted to the femoral neck in an angle of about 95–110 degrees in respect with an axial line of the femoral shaft so that an inferior screw of said three lag screws is positioned in a direction of an the inferior quadrant of the femoral head so as to slightly touch a strong portical bone of a calcar fermort of the fermoral neck.

7. The internal fixation device as claimed in claim 1, wherein said lag screws are adapted to penetrate an inferior quadrant of the femoral head, preferable distally of the terse ligament vasoutarity.

8. The internal fixation as claimed in claim 1, wherein said at least one first passage is provided with bone substitutes allowing bone grafting into said tubular member.

9. The internal fixation device as claimed in claim 1, wherein said fixation device further interlocked with an external fixator.

10. A hybrid interlocking fixation apparatus for fixating a fracture in the fermoral neck or the perltrochanteric region, the apparatus comprising:
   a tubular member having a sharp end and a blunt end;
   at least one passage provided in said tubular member wherein said at least one passage extends from said sharp end to said blunt end;
   at least one screw adapted to pass through said at least one passage and extend outwardly beyond said sharp end;
   at least two bores are lateraliy provided on said tubular member wherein said another at least two bores are provided on opposite sides of said tubular member;
   at least four pin screws wherein at least two pin screws of the four are adapted to interlock said tubular member and another at least two pin screws of the four are nailed in a distal bone fragment so as to assure stability of the tubular member within the bone;

a connecting member adapted to secure said at least four pin screws together;

whereby said tubular member is implanted in the femoral neck said at least one screw is inserted through said at least one passage so that compression end slidlng of the fractured fragments is maintained, at least one pin screw is nailed through said tubular member through said at least two bores and at least two pin screws are pined in said distal bone fragment wherein the pin screw are interconnected by said connecting member in order to facilitate the healing process and wherein said connecting member's connections can be corrected post-operatively.

11. The apparatus as claimed in claim 10, wherein three passages are provided in a sidewall of said tubular member.

12. The apparatus as claimed in claim 11, wherein three lag screws are provided to pass through said three passages.

13. The apparatus claimed in claim 10, wherein are bores are provided in said tubular tube wherein said six bores are organized so that three of the six bores are provided opposite other three of said six bores and wherein three pin screws are adapted to be inserted through said six bores from one said of said tubular member another side.

14. The apparatus as claimed in claim 10, wherein said connecting member comprises two clamps and rotating screwing rods, and wherein one clamp clamps the screw pins that are nailed to the distal bone fragment and a second clamp clamps the screw pins that are screwed into said tubular member.

15. The apparatus as claimed in claim 14, wherein a distance between said one clamp said second clamp is changeable by rotation of said rotating screwing rods that are connected to each clamp by two bolts having spherical head wherein said rotating screwing rods are screwed onto said two bolts.

16. The apparatus as claimed claim 10, wherein mal-posltioning of the hybrid interlocking fixation is corrected in intra and post-operative period.

17. The apparatus as claimed in claim 12, wherein said tubular member is provided with a plurally of small wall holes.

18. The apparatus as claimed in claim 10, wherein the apparatus is provided with radiolucent materials or other metals.

19. The apparatus as claimed in claim 10, wherein the apparatus can be disposable.

20. The apparatus as claimed in claim 10, wherein said tubutar member us provided with bone subtitles allowing bone grafting into said tubular member.

* * * * *